United States Patent [19]

Taylor

[11] Patent Number: 4,657,553

[45] Date of Patent: Apr. 14, 1987

[54] CHEMICAL SUBSTANCES

[76] Inventor: David E. M. Taylor, Royal College of Surgeons of England, 35/43 Lincoln's Inn Fields, London WC2A 3PN, England

[21] Appl. No.: 758,060

[22] Filed: Jul. 23, 1985

[30] Foreign Application Priority Data

Jul. 24, 1984 [GB] United Kingdom ............... 8418772

[51] Int. Cl.$^4$ .............................................. A61F 2/00
[52] U.S. Cl. .................................................... 623/66
[58] Field of Search ................ 623/66, 7, 8, 11, 16; 260/123.7

[56] References Cited

U.S. PATENT DOCUMENTS

| | | | |
|---|---|---|---|
| 3,882,858 | 5/1975 | Klemm | 623/66 |
| 4,349,470 | 9/1982 | Battista | 623/16 |
| 4,380,569 | 4/1983 | Shaw | 623/7 |

*Primary Examiner*—Gregory E. McNeill
*Attorney, Agent, or Firm*—Bernard, Rothwell & Brown

[57] ABSTRACT

The invention provides soft tissue implants, for the replacement and/or enhancement of human or animal soft tissue, composed of a hydrogel comprising (a) a gelable polysaccharide and/or protein or polypeptide and (b) a polymer of a hydrophilic acrylic and/or methacrylic acid derivative.

8 Claims, No Drawings

CHEMICAL SUBSTANCES

This invention relates to aqueous gels and their use as soft tissue implants.

Soft tissue implantation is now a relatively new surgical technique for replacement of fatty tissues, fibrous tissue sheets and/or muscle removed by surgery or for remodelling soft tissues such as the breasts if these are thought to be inadequate. The materials which have been used hitherto have included silicone rubber and expanded polytetrafluorethylene. Certain gels having a consistency and firmness resembling that of normal fatty tissue have been proposed but are of inadquate mechanical strength. A prosthesis of calculated size and shape prepared from such material is carefully inserted beneath intact skin or muscle to produce the required reshaping and the incision is then closed.

In the period immediately after healing of the incisions, the implant gives a realistic impression of healthy human tissue beneath the overlying skin. However, tissue reaction commonly sets in quite rapidly, with the progressive formation of a fibrous interface between the prosthesis and the surrounding tissue. Such fibrous tissue is commonly either more rigid than the implant or is contractile and so compresses the implant with a consequent increase in its rigidity. This may even, for a time, be thought to enhance the desired remodelling, particularly in the case of breasts, where a firm shape is valued. However, the rigidity of the prosthesis eventually becomes noticeable in producing pronounced ridges and the lack of resilience also emphasises the unnatural appearance of the reshaped breast. This is generally found to be psychologically disturbing to the patient.

Indeed, reshaping of breasts by soft tissue implant surgery has met with criticism partly because the eventual rigidity of the implant effectively masks any hardening due to carcinoma, so making routine testing for breast cancer difficult or impossible.

We have now found a material which is particularly suitable for use in soft tissue implantation. After subcutaneous, intramuscular and intraperitonal implantation in experimental animals over a six month period or longer, the tissue reaction which has been observed is significantly less than that with the common implant materials in clinical use.

Thus, in general, the capsule surrounding the implant is thinner than that found with comparable implants of silicone rubber and expanded polytetrafluorethylene and the collagen in the capsule is well packed and structured, in general being more flexible and less attached to surrounding tissue. The incidence of fibroblasts, mononuclear cells and giant cells is also lower.

The present invention extends to soft tissue implants composed of a hydrogel comprising (a) a gelable polysaccharide and/or protein or polypeptide and (b) a polymer of a hydrophilic acrylic or methacrylic acid derivative.

Such gels can readily be prepared having a critical surface tension and surface free energy approximating to the optimum for biotolerance. The contact angle with water is small being less than 30°. This is, in part, because the water content of such a hydrogel can be very high, for example in the range 95 to 98% by weight, preferably about 97%. Thus, the solid matrix of the gel may constitute only 2 to 5% by weight of the gel, preferably about 3%.

The hydrogel preferably comprises the gelable polysaccharide, polypeptide or protein and the (meth)acrylic polymer in the ratio range 9:1 to 1:9 by weight, preferably in the range 1:9 to 4:6.

The hydrogels are preferably of the type described in United Kingdom Patent Specification No. GB-A-1594389. Thus the hydrophilic acrylic or methacrylic acid derivative is preferably an amide, more preferably acrylamide, or an ester with an alkanol, optionally a polyol, especially preferably a $C_{1-6}$ alkanol such as methanol or ethanol. Conventional bi- or polyfunctional cross-linking agents such as N,N'-methylene-bis-acrylamide may be used to cross-link the polymer.

The gelable polysaccharide is preferably agarose or agar-agar while amongst gelable proteins and polypeptides, gelatine is preferred.

In general, the most preferred hydrogels comprise (a) agar-agar together with (b) polyacrylamide cross-linked with about 2% by weight of N,N'-methylene bis-acrylamide, advantageously in the ratio range 1:3 to 1:4, preferably about 1:3.5. This gel, when fully swollen with water, contains about 96.5% by weight of water. A gel of this type is now commercially available from Geistlich Pharma of Wolhusen, Switzerland under the Registered Trade Mark Geliperm.

It should be noted that agar-agar gels are commonly hard and brittle. On the other hand, polyacrylamide gels, even when cross-linked, are relatively soft and tacky. The above hydrogels containing both these materials are, however, nontacky and of a consistency remarkably close to that of the human tissues to be replaced or remodelled.

Thus, the elastic modulus of the hydrogel material is in the same range as that of the tissues it is designed to replace. In order to achieve such an elastic modulu for silicone breast implants it is necessary to employ a composite of an outer case of silicone rubber containing silicone fluid. Expanded polytetrafluoroethylene is a firmer although stronger material which is primarily used to replace fascia and other sheet-like tissues.

The above hydrogels are also surprisingly strong and are in general well able to withstand the stresses to which they are subjected by body movement. Many previously used materials have shown some tendency to break up under such stresses. The tensile strength at break of a test strip of the preferred agar-agar/polyacrylamide gel 3.3 mm thick and 20 mm wide is 2–3 Newtons Elongations in the range 75 to 150% have been observed, even after storage of the material for as long as 2.5 years. It seems possible that the polyacrylamide may prevent crystallisation of the agarose, thus avoiding hardness, while some measure of cross-linking may take place between the agar and the polyacrylamide which increases the strength of the material. However, if necessary, as described in United Kingdom Patent Specification No. GB-A-1594389, strengthening reinforcements can be incorporated in the gel, for example, fibres or meshes.

The hydrogels for use according to the invention may be prepared in the way described in the above United Kingdom Patent Specification. Thus, an aqueous solution of the gelable polysaccharide or protein or polypeptide may be mixed with an aqueous solution of the hydrophilic monomer to be polymerised, e.g. acrylamide, if desired together with cross-linking agent, and polymerisation may then be initiated. The two components thus form a substantially homogenous matrix or lattice. The hydrogel so formed is then washed thoroughly to remove all unreacted materials. During this washing step, the hydrogel will normally absorb water until it reaches equilibrum. It will be appreciated that when a prothesis of such material is implanted, it will reach equilibrium with the water and dissolved materials in the surrounding tissue fluid. It is possible therefore, that the prosthesis could be prepared from hydrogel containing less than the equilibrum quantity of water and that a moderate increase in volume could be allowed to take place subsequently by equilibration with water from the surrounding tissues. United Kingdom Patent Specification No. GB-A-203042 describes the removal of water from the hydrogels of United Kingdom Patent Specification No. GB-A-1594389 and the present invention includes implantation of hydrogels having less than the equilibrum concentration of water prepared by such methods.

If desired, the water in the prosthesis may contain dissolved substances, such as salts, e.g. to render the gel isotonic, as well as antibacterials to reduce infection and/or antiinflammatories to reduce inflammation following surgery.

The preparation of the prosthesis from the hydrogel may be accomplished by shaping techniques employed with previously used materials. Thus, for example, in the case of breast prostheses, moulds can be made in which a hydrogel implant of the desired profile may be cast. In general, a series of standard sizes may be available for selection of the appropriate implant by the surgeon. In the case of plastic surgery, for example of the face, implants may comprise strips of the material cut to size by the surgeon during surgery. In the case of muscle implants, relatively large blocks of the hydrogel may be shaped by the surgeon immediately prior to implantation.

It should be noted that while soft tissue implants have previously been introduced as a replacement and/or enhancement of fatty tissue or fascia tissue, no material has previously been successful for replacement of muscle tissue. We have surprisingly found that significant blocks of muscle tissue can successfully be replaced and after recovery of the subject from surgery, the implant is barely palpable and hypertrophy of surrounding muscle may compensate for the lost muscle tissue. The formation of scar tissue is minimal, so that there is little or no interference by the prosthesis with normal muscular activity.

In the case of breast prostheses, conventional surgical techniques may be used. Thus, for replacement, e.g. after mastectomy, the outer dermal tissues will have been cut in such a way as to minimise unsightly scarring and after removal of the original fatty tissue, an appropriate hydrogel prosthesis may be slipped into place and the incesions closed. For enhancement, it may be preferable to implant the prosthesis behind the original breast tissue, between the major and minor pectoral muscles.

The following Example is given by way of illustration only:

EXAMPLE 20 g of agar-agar are suspended under agitation in 880 g of deionized water and heated to 95° C. until complete dissolution. 1 l of a second aqueous solution containing 70 g of acrylamide and 1.84 g of N,N'-methylene-bis-acrylamide is prepared at ambient temperature and added to the first solution with thorough mixing. Under continued agitation, 2.2 g of N,N,N',N'-tetrakis-(2-hydroxypropyl)-ethylene diamine dissolved in 60 g of water and then 1.26 g of ammonium peroxidisulfate dissolved in 40 g of water are added.

The mixture has a temperature between 50° C. and 55° C. and begins to polymerize immediately. After 10 minutes the gel point is reached. The batch is allowed to cool down overnight during which time polymerization is completed.

The gel is freed from soluble impurities by washing with pure flowing water for 24 hours. With this washing the gel swells to 135% of its original weight. This product is now commercially available under the name Geliperm from Geistlich Pharma of Wolhusen, Switzerland.

The gel may then be shaped to form a prosthesis and used as a tissue implant by known surgical techniques.

(a) Biotolerance Studies

Experiments have been carried out in the rat; to assess biotolerance after six week implantation, to assess biotolerance after six months, to assess possible long term biodegradation, and to determine whether delayed hypersensitivity occurred.

Material and Methods

The Geliperm was in strip form and was implanted in the fully hydrated state. Test implants were approximately $5 \times 5 \times 3$ mm.

The experimental animals were adult PortonWistar rats of weight 250–350 g.

The six week and six months biotolerance studies were carried out on 8 and 10 animals respectively, while the other two studies each involved 6 animals. In all studies three implant sites were used, intramuscular into the sacrospinalis, subcutaneous into the lateral abdominal wall and intraperitoneal.

For the biotolerance studies two control materials were also studied after six weeks implantation in 8 animals each: polydimethylsiloxane (Silastic (Registered Trade Mark) Dow Corning Inc.) and expanded microporous polytetrafluoraethylene (Gore-Tex (Registered Trade Mark) W. L. Gore Associates). These were selected as materials of proven good biotolerance in the intended field of application and in current clinical use.

Biotolerance was assessed by quantitative histology for capsule thickness, cellular infiltrate density and collagen organisation.

For the biodegradation studies the test samples of Geliperm were dehydrated and weighed under sterile conditions, then rehydrated before implantation. At the end of the test period the recovered implants were again dehydrated and weighed. This was to avoid errors due to variation of water-content of the hydrogel.

For the delayed hypersensitivity test after six weeks implantation at the three standard sites, the skin of the back was shaven and test patches of Geliperm and a control moist gauze swab applied to the back for 72 hours. The animal was then sacrificed and after macroscopic examination the skin of the back was assessed histologically for oedema, inflammation and lymphocyte or other cellular infiltration.

Results

There was no macroscopically inappropriate response to Geliperm at either six weeks or six months implantation: indeed of the peritoneal implants many were free within the peritoneal cavity, although encapsulated. All the six week control materials were invested in bowel or peritoneum and strongly bound with adhesions.

At 6 months the capsule thickness around the Geliperm was not significantly different from that at six weeks being less than 50 microns. The collagen of the capsule was well packed and oriented parallel to the implant interface. The capsule thickness was significantly less than that surrounding the Silastic implants and slightly less than that of the Gore-tex implants. The incidence of fibroblasts, monocuclear cells and giant cells was lower in the case of Geliperm than the control materials.

There was no evidence of significant biodegradation at three months and no evidence of skin sensitivity developing.

(b) Reconstructive Surgery Studies: rats

Two studies were carried out in the rat: in the first a large muscle defect in the sacrospinalis muscle in the lumbar region was replaced with polyacrylamideagarose and the fascia closed over it, while in the second a pair of "breast implants" were placed subcutaneously or retropectoral in the anterior thoracic region. The muscle implants were studied after six weeks and six months. There was no functional disability in the animals and the implant site was not palpable through the skin in life. There was a minimal fibrous capsule (<70 um) around the implant and there appeared to be hypertrophy of surrounding muscle. The "breast implants" also showed little fibrous capsule formation and had not changed appreciably in consistance when examined at up to three months after implantation. With both long term implants there was little evidence of a chronic inflammatory reaction persisting and giant cells were virtually absent.

(b) Reconstructive Surgery Studies: dogs

In a pilot study large (26 and 53 g) defects of the sacrospinalis muscle were made in 2 dogs and replaced with Geliperm shaped from 13 mm thick sheets. Both healed well and showed good resolution. The defects were not palpable and the animals had a normal range and strength of movement.

In a further dog two subcutaneous blocks, each of about 50 g in weight, of Geliperm were placed subcutaneously in the back, one superficial and the other deep to platysma. After two months the wounds were well healed with no residual induration. The most superficial implant was palpable, but soft and mobile with the subcutaneous tissue. The implant deep to platysma could be distinguished by palpation.

I claim:

1. Soft tissue implants, for the replacement and/or enhancement of human or animal soft tissue, composed of a hydrogel comprising (a) a gelable polysaccharide and/or protein or polypeptide and (b) a polymer of a hydrophilic acrylic and/or methacrylic acid derivative.

2. Implants as claimed in claim 1 in which the hydrogel comprises (a) agar-agar (agarose) and (b) cross-linked polyacrylamide.

3. Implants as claimed in claim 2 in which the ratio of component (a) to component (b) is in the range 1:3 to 1:4.

4. Implants as claimed in claim 1 which the water content of the hydrogel is 95 to 98% by weight.

5. Implants as claimed in claim 1 in the form of breast-shaped prostheses.

6. A method of replacement and/or enhacement of human or animal soft tissue which comprises implanting a prosthesis composed of a hydrogel as defined in claim 1 is implanted in a soft tissue region of the human or animal body.

7. A method as claimed in claim 6 in which the prosthesis is breast shaped and is implanted below the skin and/or other tissue of the human female breast to replace and/or enhance the fatty tissue of the breast.

8. A method as claimed in claim 6 in which the prosthesis is implanted intramuscularly to replace muscle removed by injury and/or surgery.

* * * * *